United States Patent
Vicik

(10) Patent No.: US 6,632,635 B1
(45) Date of Patent: Oct. 14, 2003

(54) METHODS OF REFOLDING PROTEINS

(75) Inventor: Steven M. Vicik, Boxborough, MA (US)

(73) Assignee: Genetics Institute, Cambridge, MA (US)

( * ) Notice: Subject to any disclaimer, the term of this patent is extended or adjusted under 35 U.S.C. 154(b) by 0 days.

(21) Appl. No.: 09/575,273

(22) Filed: May 22, 2000

Related U.S. Application Data

(62) Division of application No. 08/946,839, filed on Oct. 8, 1997.

(51) Int. Cl.[7] .............. C12P 21/00; C07K 14/495; C07K 14/51; C12N 1/21; C07H 15/22
(52) U.S. Cl. .............. 435/69.1; 435/252.3; 435/252.33; 530/350; 564/462
(58) Field of Search .............. 435/69.1, 252.3, 435/252.33; 530/350; 562/30, 400; 564/462

(56) References Cited

U.S. PATENT DOCUMENTS

| | | | |
|---|---|---|---|
| 5,013,649 A | | 5/1991 | Wang et al. |
| 5,106,748 A | | 4/1992 | Wozney et al. |
| 5,116,738 A | | 5/1992 | Wang et al. |
| 5,141,905 A | | 8/1992 | Rosen et al. |
| 5,187,076 A | | 2/1993 | Wozney et al. |
| 5,399,677 A | * | 3/1995 | Wolfman et al. ............ 530/350 |
| 5,407,810 A | * | 4/1995 | Builder et al. ............. 435/69.1 |
| 5,635,372 A | | 6/1997 | Celeste et al. |
| 5,650,494 A | | 7/1997 | Cerletti et al. |
| 5,663,304 A | * | 9/1997 | Builder et al. ............ 435/252.3 |

FOREIGN PATENT DOCUMENTS

| | | |
|---|---|---|
| EP | 226 448 | 6/1987 |
| EP | 433 225 | 6/1991 |
| JP | 7250688 | 3/1995 |
| WO | WO91/18098 | 11/1991 |
| WO | WO93/00432 | 1/1993 |
| WO | WO93/16099 | 8/1993 |
| WO | WO93/19229 | 9/1993 |
| WO | WO94/01557 | 1/1994 |
| WO | WO94/15949 | 7/1994 |
| WO | WO94/15965 | 7/1994 |
| WO | WO94/15966 | 7/1994 |
| WO | WO94/21681 | 9/1994 |
| WO | WO94/26892 | 11/1994 |
| WO | WO94/26893 | 11/1994 |
| WO | WO95/01801 | 1/1995 |
| WO | WO95/01802 | 1/1995 |
| WO | WO95/10539 | 4/1995 |
| WO | WO95/16035 | 5/1995 |
| WO | WO95/19339 | 7/1995 |
| WO | WO96/01845 | 1/1996 |
| WO | WO96/02559 | 2/1996 |

OTHER PUBLICATIONS

Hotten et al. Cloning and expression of recombinant human growth/differentiation factor 5. Biochem Biophys Res Commun. Oct. 28, 1994;204(2):646–52.*
Kohno, Methods Enzym. 185: 187–95 (1990).
Goldberg, Folding Design, 1: 21–27 (1996).
Jones, Mol. Endocrinol. 6: 1961–68 (1992).
Thies, J. Bone and Min. Res. 5(2): 305 (1990).
Thies, Endocrinology 130: 1324 (1992).
Ullman, Biochem. And Biophys. Res. Comm. 35(1): 35–42 (1969).
Holzman, Biochemistry 25 (22): 6907–17 (1986).
Marston, Biochem. J. 240(1): 1–12 (1986).
Daopin, Science 257: 369–73 (1992).
Tandon & Horowitz, J. Biol. Chem. (10) 262: 486–91 (1987).

* cited by examiner

*Primary Examiner*—David S. Romeo
(74) *Attorney, Agent, or Firm*—Fitzpatrick, Cella, Harper & Scinto

(57) ABSTRACT

Methods are disclosed for refolding proteins of the TGF-β family of proteins. The methods employ as refolding agents one or more compounds which are acid substituted aminocyclohexanes.

5 Claims, No Drawings

METHODS OF REFOLDING PROTEINS

This application is a divisional application of co-pending U.S. patent application No. 08/946,839 filed Oct. 8, 1997.

The present invention relates to methods of refolding proteins, particularly protein members of the transforming growth factor beta ("TGF-β") superfamily of proteins, such as the bone morphogenetic proteins ("BMPs"). These methods are particularly useful in improved processes for preparation of biologically active dimeric recombinant bone morphogenetic proteins produced in insoluble form from bacterial cell cultures.

BACKGROUND OF THE INVENTION

A number of proteins referred to in the art as bone morphogenetic proteins have recently been identified which are able to induce bone or cartilage formation when implanted into mammals. For example, Wang et al. in U.S. Pat. No. 5,013,649, incorporated herein by reference, describe the DNA sequences encoding bovine and human bone morphogenetic proteins 2A (now bone morphogenetic protein-2) and 2B (now bone morphogenetic protein 4), the corresponding proteins encoded by those DNA sequences, and processes for recombinant production of the BMP-2A (now BMP-2) and BMP-2B (now BMP-4) proteins. These proteins are expected to have broad medical applicability in treatment of bone and cartilage injuries and disorders in mammals. In order to fulfill the expected medical need for these bone morphogenetic proteins, large quantities of biologically active protein will be needed.

Recombinant production of the bone morphogenetic proteins is possible both in eukaryotic and prokaryotic cell culture systems. A common occurrence in recombinant production of heterologous proteins in prokaryotic cells, such as bacteria, is the formation of insoluble intracellular precipitates known as inclusion bodies. While the bacteria are generally able to transcribe and to translate DNA sequences encoding heterologous proteins correctly, these prokaryotic cells are unable to fold some heterologous proteins sufficiently correctly to allow for their production in a soluble form. This is particularly true of prokaryotic expression of proteins of eukaryotic origin, such as the bone morphogenetic proteins. Formation of incorrectly folded heterologous proteins has to some extent limited the commercial utility of bacterial fermentation to produce recombinant mammalian proteins. When produced in bacteria, the recombinant bone morphogenetic proteins are often similarly found in inclusion bodies in an aggregated, biologically inactive form.

Several methods for obtaining correctly folded heterologous proteins from bacterial inclusion bodies are known. These methods generally involve solubilizing the protein from the inclusion bodies by denaturing the protein using acids or a chaotropic agent. Subsequently, protein is diluted into a refolding buffer that supports renaturation to a biologically active form. When cysteine residues are present in the primary amino acid sequence of the protein, it is often necessary to accomplish the refolding in an environment which allows correct formation of disulfide bonds (a redox system). General methods of refolding are disclosed in Kohno, *Meth. Enzym.*, 185:187–195 (1990).

EP433225 describes a method for refolding transforming growth factor β (TGF-β)-like proteins which employs, in addition to a chaotropic agent and a redox system, a solubilizing agent in the form of a detergent. EP433225 predicts that the methods disclosed therein are generally applicable for refolding "TGF-β-like proteins", based on the degree of homology between members of the TGF-β family. However, the present inventors have found that the methods disclosed in EP433225 produce undesirably low yields of correctly folded, biologically active dimeric protein when applied to numerous bacterially produced BMPs. In addition, the methods disclosed employ 3-[(3-cholamidopropyl) dimethylammonio]-1-propanesulfonate (CHAPS) and other expensive compounds as the solubilizing agent.

Non-detergent sulfobetaines have been used in attempts to renature hen egg white lysozyme (HEWL) and β-D-galactosidase. However, these attempts have not been very effective and have practical drawbacks, such as yield. For example, certain sulfobetaines reduced the yield of β-D-galactosidase by a factor of 100-fold. Goldberg et al., *Folding Design.*, 1:21–27 (1996). Accordingly, these molecules have not been shown to be broadly effective as refolding agents, particularly for use in refolding multimeric proteins such as TGF-β proteins.

SUMMARY OF THE INVENTION

It has been found, unexpectedly, that the dimeric proteins of the TGF-β superfamily, and particularly, bone morphogenetic proteins (BMPs), can be efficiently produced and refolded from bacterial cultures, such as *E. coli*, using methods which employ as refolding agents non-detergent nitrogen-containing compounds for the renaturation and correct refolding of dimeric protein. Among the compounds useful in the present invention are members of the non-detergent zwitterions, pyridines, pyrroles and acid substituted aminocyclohexanes.

Accordingly, in one embodiment, the invention comprises methods of producing properly refolded proteins of the TGF-β superfamily from bacterial cell cultures using a non-detergent compound as a reagent in the method. The bacterial cell culture is preferably *E. coli*, but may be another bacterial or prokaiyotic cell culture type. The protein may be any protein from the TGF-β superfamily, and is preferably a member of the BMP family, or the growth and differentiation factors ("GDFs"), as well as MP52 and other proteins as described further herein. The non-detergent compound may be nitrogen-containing and/or zwitterionic, and preferably includes an aromatic or aliphatic ring, is preferably nitrogen containing, and is preferably substituted with a substituent which includes an electrophilic or electron accepting end group, such as a carboxyl or sulfhydryl group. Other end groups which may be useful in the present invention include amide groups. The non-detergent compound is preferably selected from the group consisting of sulfobetaines, pyridines, pyrroles and aminocyclohexanes.

The non-detergent zwitterions useful in the present methods include sulfobetaines and pyridinium propanesulfonates, such as 3-(1-pyridinio)-1-propanesulfonate ("3-1-PPS"). Pyridine compounds useful in the present invention are preferably acid or amide substituted, and include pyridine 3-sulfonic acid, pyridine-2 carboxylic acid [also known as nicotinic acid or niacin or Vitamin B], picolinic acid, 3-pyridylacetic acid hydrochloride, 4-pyridylacetic acid hydrochloride, isonicotinic acid and nicotinamide. Pyrrole compounds which are useful in the present invention include the pyrrole analog of the above pyridine compounds. For example, pyrrole-2 carboxylic acid, the pyrrole analog of nicotinic acid, is effective in the methods of the present invention. Other non-detergent zwitterionic compounds useful in the present invention are compounds with a nitrogen containing aromatic ring, further containing an electron accepting substituent group, such as N-methyl-N-piperidine propane sulfonic acid, trigonelline hydrochloride, and 1-carboxymethyl pyridinium chloride.

Unlike pyridines and pyrroles, acid substituted aminocyclohexane compounds which are useful in the present invention contain an aliphatic ring with an amine substituent with an electron accepting group, such as a carboxyl or sulfhydryl group. For example, 2-aminocyclbhexane carboxylic acid, 3-(cyclohexylamino)-1-propanesulfonic acid (CAPS), 3-cylclohexylamino)-2-hydroxypropanesulfonic acid (CAPSO) and 2-(cylcohexylamino)ethanesulfonic acid (CHES) are each effective in the methods of the present invention.

The methods of the present invention are further advantageous in that many of these compounds are relatively inexpensive and commercially available. For example, 3-1-PPS is commercially available from Fluka Chemical Company, while Vitamin B is widely manufactured as a dietary supplement and food additive.

DETAILED DESCRIPTION OF THE INVENTION

Among the proteins which may be produced recombinantly using the methods of the present invention are: BMP-2, BMP-3, BMP-4, BMP-5, BMP-6 and BMP-7, disclosed for example in U.S. Pat. Nos. 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, BMP-12 or BMP-13, disclosed in PCT application WO 95/16035, or BMP-15, disclosed in U.S. Pat. No. 5,635,372. Other proteins of the TGF-β superfamily which may be produced by the methods of the present invention include Vgr-2, disclosed in Jones et al., *Mol. Endocrinol.*, 6:1961–1968 (1992); BIP, disclosed in WO94/01557; HP00269, disclosed in JP Publication number. 7-250688; and MP52, disclosed in PCT application WO93/16099, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. The methods of the present invention may be used to produce commercial scale quantities of BMP homodimers or heterodimers from bacteria and refolded into biologically active dimeric molecules. Production of heterodimers of BMPs is described, for example, in WO93/19229. The disclosures of all of the above applications are hereby incorporated by reference.

Any bacterial species may be used to generate recombinant BMP for refolding in the method of the invention. Preferably, *Bacillus subtilis*, Pseudomonas or *Escherichia coli* is used to produce inclusion bodies containing BMP. Most preferably, *Escherichia coli* is used to produce inclusion bodies containing BMP for refolding in the method of the invention. Any strain of *E. coli* may be used to produce BMP for refolding in the method of the invention, so long as that strain is capable of expression of heterologous proteins. One preferred strain, *E. coli* strain G1724 (A.T.C.C. accession number 55151) or GI774 [without thyA] may be used to produce BMP for refolding in the method of the invention.

The methods of the present invention may be used to produce BMPs in bacteria using known methods. It may be necessary to modify the N-terminal sequences of the BMP in order to optimize bacterial expression. For example, because cleavage of the bond between formyl-methionine and glutamine is inefficient in *E. coli*, the N-terminus of the native mature BMP-2 protein (Met-gln-ala-lys) is modified by deletion of the glutamine residue to yield an N-terminus more suitable for BMP-2 production in *E. coli* (Met-ala-lys-his). Other bacterial species may require analogous modifications to optimize the yield of the mutant BMP obtained therefrom. Such modifications are well within the level of ordinary skill in the art.

The modified or unmodified nucleotide sequence which encode BMPs may be inserted into a plasmid suitable for transformation and expression of those heterologous proteins in bacteria. Any bacterial expression plasmid may be used, so long as it is capable of directing the expression of a heterologous protein such as BMP in the bacteria chosen. Acceptable species of bacteria include *B. subtilis*, species of Pseudomonas, and *E. coli*. Suitable expression plasmids for each of these species are known in the art. For production of BMP in bacteria, a suitable vector is described in Taniguchi et al., *Proc. Natl. Acad. Sci.*77:5230–5233 (1980).

The bacterial expression plasmid may be transformed into a competent bacterial cell using known methods. Transformants are selected for growth on medium containing an appropriate drug when drug resistance is used as the selective pressure, or for growth on medium which is deficient in an appropriate nutrient when auxotrophy is used as the selective pressure. Expression of the heterologous protein may be optimized using known methods. The BMP thus obtained will be present in insoluble, refractile inclusion bodies which may be found in pellets of disrupted and centrifuged cells.

The inclusion bodies thus obtained may be solubilized using a denaturant such as guanidine hydrochloride or by acidification with an acid such as acetic acid or formic acid. If solubilized using a denaturant, a reducing agent such as $-mercaptoethanol, glutathione, or dithiothreitol is added with the denaturant. If the protein is solubilized by acidification, it must be reduced prior to acidification.

Prior to refolding, the solubilized heterologous protein may be further purified using known chromatographic methods such as size exclusion chromatography or reverse phase high performance liquid chromatography. The solution containing the BMP may then be reduced in volume or vacuum desiccated to remove chromatography buffer and redissolved in medium. Alternatively, reduced soluble protein may be renatured by diluting into refolding medium. For example, suitable media may include the following:

(a) 50 mM Tris;

(b) 1.0 M NaCl;

(c) 0.7M 2-(cyclohexylamino)ethanesulfonic acid (CHES) or 1.0 M 3-(1-pyridinio)-propanesulfonate (3-1-PPS) or 0.4 M pyrrole-2 carboxylic acid or 0.70 M nicotinic acid;

(d) 5 mM EDTA;

(e) 2 mM gluatathione (reduced);

(f) 1 mM glutathione (oxidized);

(g) at pH of approximately 8.5

Other media may be suitable for renaturation, including media containing low levels of the chaotrope (e.g., guanidine hydrochloride) or the salt of the acid (e.g. acetate) used to solubilize the BMP inclusion bodies. Refolding is typically conducted at a BMP concentration of 1 to 100 µg/ml protein. Higher concentrations of protein may be refolded in accordance with the invention, for example up to about 1 mg/ml, but precipitates or aggregates may be present above protein concentrations of 100 μg/ml and the yield of active BMP homodimer or heterodimer may be decreased accordingly.

For production of heterodimers, the above procedure is performed utilizing equal amounts of two plasmids, each containing a coding sequence for a distinct BMP (e.g., pALBP2, encoding BMP-2 and pALBPX encoding BMP-X, where X is a BMP other than BMP-2). The plasmids are cultured separately, and the resulting inclusion bodies are solubilized and refolded in accordance with the methods described herein. The refolded protein monomers are mixed together in equivalent ratios and treated as described in the paragraph above. The resulting dimeric proteins are observed to include homodimers of BMP-2, as well as heterodimers of BMP-2/X. These species may be separated out from each other through procedures known in the art.

In order to refold the proteins, the following conditions and media may be used: about 10 mM to about 100 mM Tris or other suitable buffer, preferably about 50 mM Tris, about 0.1 to about 4.0 M NaCl or other suitable salt, preferably about 1.0 M NaCl, about 0.05 to about 2.0 M refolding agent [non-detergent zwitterion, sulfobetaine, pyridine, pyrrole, or aminocyclohexane], preferably about 0.7M refolding agent, about 1 mM to about 10 mM EDTA or other suitable metal ion chelating reagent, preferably about 5 mM EDTA, a suitable redox system, such as glutathione, preferably at a ratio of about 1:10 to about 10:1 reductant to oxidant, at pH of about 7 to about 11, preferably about 8.5.

Because BMPs are disulfide bonded dimers in their active state, it is useful to include a redox system which allows formation of thiol/disulfide bonds in the method of the invention. Several such redox systems are known. For example the oxidized and reduced forms of glutathione, dithiothreitol, β-mercaptoethanol, β-mercaptomethanol, cystine and cystamine may be used as redox systems at ratios of reductant to oxidant of about 1:10 to about 10:1. When the glutathione redox system is used, the ratio of reduced glutathione to oxidized glutathione is preferably 1 to 10; more preferably 1 to 1; and most preferably 2 to 1 of reduced form to oxidized form.

In addition to the refolding agent, the method of the invention may employ a salt moiety. The salt moiety is preferably NaCl, preferably at a concentration of about 0.1M to about 2.0M, preferably about 1.0M. It may be preferable to vary the sodium chloride concentration as the concentration of refolding agent varies.

The pH of the refolding reaction of the present invention is preferably from about 7 to about 11; more preferably from about 8 to about 10 and most preferably about 8.5.

Preferably, the refolding reaction of the invention is performed at a temperature range from about 4° C. to about 37° C. More preferably, the refolding reaction is performed at 20° C. The refolding reactions of the present invention are allowed to proceed to completion between 8 and 120 hours and most preferably 96 hours.

The extent of refolding of bone morphogenetic proteins obtained is monitored by sodium dodecyl sulfate-polyacrylamide electrophoresis (SDS-PAGE) under non-reduced and reduced conditions. For example, the BMP4 homodimer will appear as a band of about 30 kD under non-reduced conditions on a 16 percent SDS-polyacrylamide gel; and the BMP4 monomer appears as a band of about 13 kD under reduced conditions. The BMP-2/5 heterodimer will appear as a band of about 35 kD under non-reduced conditions on a 16 percent SDS-polyacrylamide gel; the BMP-2 monomer appears as a band of about 13 kD under reduced conditions; and the BMP-5 monomer appears as a band of about 15 kD under reduced conditions. The BMP-2/6 heterodimer will appear as a band of about 35 kD under non-reduced conditions on a 16 percent SDS-polyacrylamide gel; the BMP-2 monomer appears as a band of about 13 kD under reduced conditions; and the BMP-6 monomer appears as a band of about 15 kD under reduced conditions. The BMP-2/7 heterodimer will appear as a band of about 35 kD under non-reduced conditions on a 16 percent SDS-polyacrylamide gel; the BMP-2 monomer appears as a band of about 13 kD under reduced conditions; and the BMP-7 monomer appears as a band of about 15 kD under reduced conditions.

Without limiting the invention to a particular theory or mode of action, a unifying concept for the compounds which are useful in the present invention appears to be molecules which contain a combination of two domains, usually nitrogen-containing molecules. First, the molecule should contain a hydrophobic domain, for example, an aromatic ring such as a pyridine or pyrrole ring. Alternatively, it may be a non-aromatic ring such as cyclohexane or a non-aromatic nitrogen containing ring in which nitrogen is in the form of a quaternary amine, such as N-methyl-N-piperidine propane sulfonic acid (also known as 1-methyl-1-sulfonylpropyl piperidine). Second, the molecule should contain a substituent domain(s) which provides either zwitterionic or anionic attributes to the molecule. In a preferred embodiment, the substituent domain renders the molecule zwitterionic. In addition, the hydrophobic and substituent domains of the molecule should preferably be separated so as to present distinct regions. In a preferred embodiment, the electron accepting end group is no more than four carbons removed from the substituted aromatic or aliphatic nitrogen containing ring, more preferably no more than three carbons removed from the substituted aromatic or aliphatic nitrogen containing ring.

Accordingly, the compounds useful as refolding agents in the present methods include non-detergent zwitterionic compounds. For purposes of the present invention, it should be recognized that certain compounds may be "zwitterionic" at selected pH ranges, but not at others. Such compounds are preferably useful in the present invention at a pH in which the compound is zwitterionic. Preferred compounds in this group include non-detergent zwitterions, such as sulfobetaines, including certain pyridines and pyrroles. Substituted aliphatic nitrogen containing rings may also be useful when nitrogen is in the form of a quaternary amine. In one preferred embodiment, the non-detergent sulfobetaine zwitterion 3-(1-pyridinio)-1-propanesulfonate ("3-1-PPS"), which is commercially available from Fluka Chemical Company, is useful in the present invention.

In addition, compounds comprised of an aliphatic ring such as cyclohexane substituted with an amine group and an electron accepting substituent such as carboxyl or sulthydryl group are also effective. This class of compounds may also be referred to as acid substituted aminocyclohexanes. Included in this group of compounds are some common biological buffers, or AGood=s buffers@, including 2-(cyclohexylamino)ethanesulfonic acid (CHES), 3-(cyclohexylamino)-1-propanesulfonic acid (CAPS), 3-(cyclohexylamino)-2-hydroxypropanesulfonic acid (CAPSO). Another example of a preferred acid substituted aminocyclohexane useful in the present invention is 2-aminocyclohexane carboxylic acid.

Alternatively, compounds useful in the present methods include compounds with substituted aromatic nitrogen containing rings such as pyridines and pyrroles substituted with electron accepting groups, preferably acid groups such as carboxyl or sulfhydryl groups, or amide groups. In a preferred embodiment, the pyridine nicotinic acid, or vitamin B, is useful in the present invention. Other heterocyclic compounds, for example purines, diazines, pyrazoles and imidazoles substituted with electron accepting substituents, preferably acid groups such as carboxyl or sulfhydryl groups, or amide groups, may also be useful in the present invention, as well as derivatives of each of these compounds.

Accordingly, in one embodiment, the invention comprises methods of expressing properly refolded proteins of the TGF-β superfamily from bacterial cell cultures using one of the above refolding compounds, as described more fully below, as a reagent in the method. The bacterial cell culture is preferably *E. coli*, but may be another bacterial or prokaryotic cell culture type. The protein may be any protein from the TGF-β superfamily, and is preferably a member of the BMP family, or the growth and differentiation factors ("GDFs"), as well as MP52 and other proteins as described further herein. The refolding compound is preferably selected from the group consisting of non-detergent zwitterions, including non-detergent sulfobetaines, substituted pyridines, substituted pyrroles and acid substituted aminocyclohexanes. The refolding compound preferably comprises a hydrophobic domain, for example, an aromatic or aliphatic ring, and preferably further comprises a substituent domain, for example, an electron accepting end group, preferably an acid group such as a carboxyl or sulfhydryl group. Other substituent domains which may be useful in the present invention include amide groups. The non-detergent sulfobetaines useful in the present methods include pyridinium propanesulfonates, such as 3-(1-pyridinio)-1-propanesulfonate ("3-1-PPS"). Substituted pyridine compounds useful in the present invention include pyridine 3-sulfonic acid, pyridine-2 carboxylic acid [also known as nicotinic acid, niacin or Vitamin B], picolinic acid, 3-pyridylacetic acid hydrochloride, 4-pyridylacetic acid hydrochloride, isonicotinic acid and nicotinamide. Substituted pyrrole compounds which are useful in the present invention include the pyrrole analog of the above pyridine compounds. For example, pyrrole-2 carboxylic acid, pyrrole 3-sulfonic acid, 3-pyrrole acetic acid hydrochloride, 2-pyrrole acetic acid hydrochloride 2-pyrrole ethane sulfonic acid, 3-pyrrolehydroxymethane sulfonic acid. Among the substituted aminocyclohexanes which are useful in the present invention are 2-aminocyclohexanecarboxylic acid, and Good's Buffers, such as CHES, CAPS and CAPSO. Illustrated below are some compounds which are useful in the present invention.

Non-Detergent Zwitterions, Substituted Pyridines and Nicotinic Acid Derivatives

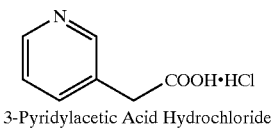
3-Pyridylacetic Acid Hydrochloride

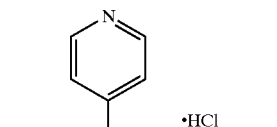
4-Pyridylacetic Acid Hydrochloride

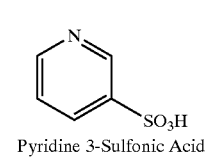
Pyridine 3-Sulfonic Acid

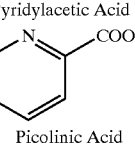
Picolinic Acid

-continued

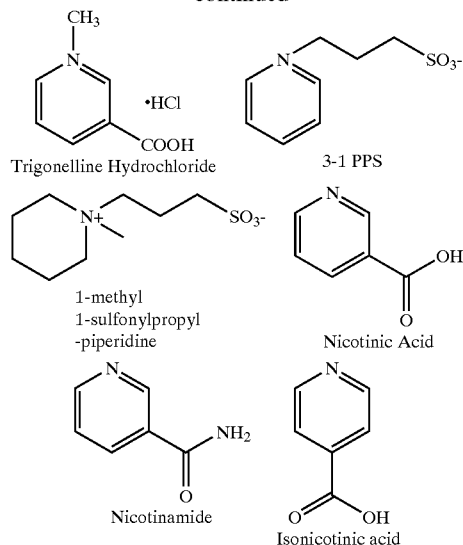

Trigonelline Hydrochloride 3-1 PPS 1-methyl 1-sulfonylpropyl -piperidine

Nicotinic Acid

Nicotinamide

Isonicotinic acid

Substituted Pyrroles

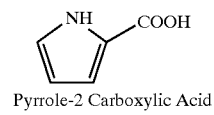

Pyrrole-2 Carboxylic Acid

Unlike the substituted pyridines and pyrroles, substituted aminocyclohexanes which are useful in the present invention contain an aliphatic ring with an amine substiuent with an electron accepting end group, such as a carboxyl or sulfhdryl group. For example, CHES, CAPS and CAPSO are each effective in the method of the present invention. Illustrated below are various compounds which are useful.

Substituted Aminocyclohexanes:

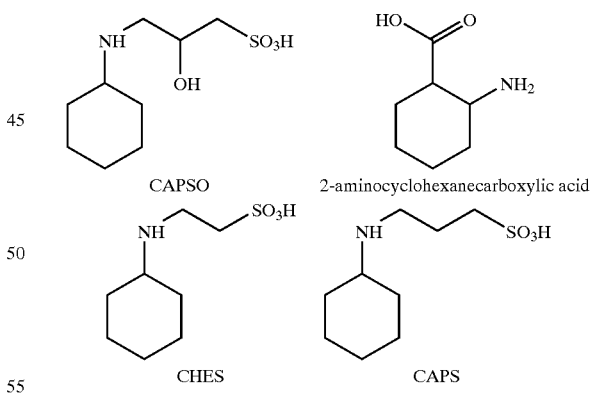

CAPSO 2-aminocyclohexanecarboxylic acid

CHES

CAPS

The in vitro biological activity of the refolded bone morphogenetic proteins may be monitored by the W-20 assay as set forth in the examples. Use of the W-20-17 bone marrow stromal cells as an indicator cell line is based upon the conversion of these cells to osteoblast-like cells after treatment with BMP [Thies et al., Journal of Bone and Mineral Research 5(2): 305 (1990); and Thies et al., Endocrinology 130: 1318–1324 (1992)]. W-20-17 cells are a clonal bone marrow stromal cell line derived from adult mice by researchers in the laboratory of Dr. D. Nathan, Children's Hospital, Boston, Mass. Treatment of W-20-17 cells with BMP results in (1) increased alkaline phosphatase production, (2) induction of parathyroid hormone stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date the conversion of W-20-17 stromal cells to osteoblast-like cells has been observed only upon treatment with bone morphogenetic proteins.

The following examples illustrate practice of the present invention in expressing and recovering recombinant human BMP-2 protein using non-detergent zwitterions, substituted pyridines, substituted pyrroles, and acid substituted aminocyclohexanes in the refolding reaction. These examples are not limiting, and the skilled artisan will recognize that numerous modifications and variations are available. Such modifications constitute part of the present invention. The disclosure of each of the publications and references referred to herein are hereby incorporated by reference for the contents thereof.

EXAMPLES

Example 1

Expression of BMP in E. coli

An expression plasmid pALBP2-781 containing the following principal features was constructed for production of BMP-2 in *E. coli*. Nucleotides 1–2060 contain DNA sequences originating from the plasmid pUC-18 [Norrander et al., *Gene* 26:101–106 (1983)] including sequences containing the gene for β-lactamase which confers resistance to the antibiotic ampicillin in host *E. coli* strains, and a colE1-derived origin of replication. Nucleotides 2061–2221 contain DNA 5 sequences for the major leftward promotor (pL) of bacteriophage λ [Sanger et al., *J. Mol. Biol.* 162:729–773 (1982)], including three operator sequences $O_L1$, $O_L2$ and $O_L3$. The operators the binding sites for λcl repressor protein, intracellular levels of which control the amount of transcription initiation from pL. Nucleotides 2222–2723 contain a strong ribosome binding sequence included on a sequence derived from nucleotides 35472 to 35566 and 38137 to 38361 from bacteriophage lambda as described in Sanger et al., *J. Mol. Biol.* 162:729–773 (1982). Nucleotides 2724–3133 contain a DNA sequence encoding mature BMP-2 protein with an additional 62 nucleotides of 3'-untranslated sequence. Nucleotides 3134–3149 provide a "Linker" DNA sequence containing restriction endonuclease sites. Nucleotides 3150–3218 provide a transcription termination sequence based on that of the *E. coli* asp A gene [Takagi et al., *Nucl. Acids Res.* 13:2063–2074 (1985)]. Nucleotides 3219–3623 are DNA sequences derived from pUC-18.

Using restriction endonucleases and procedures known in the art, one can readily replace the coding sequence for BMP-2 contained in pALBP2-781 with the coding sequence for another BMP desired to be produced in *E. coli*. With this substitution in the pALB2-781 plasmid, the following examples may be used to express and refold any of the BMPs of the present invention. If desired, additional modifications within the skill of the art can be made in the regulatory elements of the plasmid and/or cell line in order to improve or simplify the expression system.

Plasmid pALBP2-781 was transformed into the *E. coli* host strain GI724 (F⁻, lacI$^q$, lacp$^{L8}$, ampC::λcl⁺) by the procedure of Dagert and Ehrlich, *Gene* 6:23 (1979). Transformants were selected on 1.5% w/v agar plates containing IMC medium, which is composed of M9 medium [Miller, "Experiments in Molecular Genetics," Cold Spring Harbor Laboratory, New York (1972)] supplemented with 1 mM MgSO$_4$, 0.5% w/v glucose, 0.2% w/v casamino acids and 100 µg/ml ampicillin.

GI724 transformed with pALBP2-781 was grown at 32° C. to an A$_{600}$ of 15 in IMC medium with 3× MgSO$_4$ and 200 µg/ml ampicillin. For growth with other lines of *E. coli* which do not carry the thyA gene, ampicillin is not required in the medium. The glucose concentration of the culture was maintained at approximately 0.2% (wt./vol.). The pH was maintained at 7.2 with 7.5 M ammonium hydroxide. Tryptophan was added to a final concentration of 100 µg/ml and the culture was incubated for a further 4 hours at 37° C. During this time, BMP protein accumulated to approximately 10% of the total cell protein; all in the inclusion body fraction.

Example 2

Purification, Reduction, and Solubilization of BMP-2 Inclusion Bodies 4.5 kg of cells stored at −80° C. were measured. 32 L of 11 mM TRIS, pH 8.0 was added. The suspension was mixed with a rotor/stator mixer until cells were well suspended. Cells were lysed by passing the suspension through an APV Gaulin CD-30 homogenizer three times at 8500 psig. Inclusion bodies were recovered in a Sharples AS-26 centrifuge operated at maximum relative centrifugal force of 15,000×g with a feed flow rate of 0.8 L/min. Recovered inclusion bodies were combined with 35 L of 100 mM TRIS/5 mM EDTA, pH=8.0 and mixed with a rotor/stator mixer until well suspended. The inclusion body suspension was passed through an APV Gaulin CD-30 homogenizer nine times at 12,500 psig and the inclusion bodies were recovered by centrifugation in a Sharples AS-26 centrifuge operating a maximum relative centrifugal force of 15,000×g with a feed flow rate of 0.5–1.0 L/min. Approximately 340 grams of BMP-2 containing inclusion bodies were recovered. Inclusion bodies were further purified after suspension in 50 mM TRIS, pH=8.0 at 9 gram/L by centrifugation for five minutes at a maximum relative centrifugal force of 3000×g. The resulting supernatants were decanted. Inclusion bodies were solubilized and reduced by incubating in an equal volume of 8 M guanidine-HCl, 10 mM EDTA, 100 mM TRIS and 100 mM dithiothreitol, pH=8.5 for one hour at 37° C. Insoluble material was subsequently removed by filtration through a Millipore Millex 0.2 µm filter. Reduced and denatured BMP-2 monomer was further purified using a C4 reversed phase column (2.2×25 cm Vydac). The column was eluted using a linear gradient from 40 to 80% B in 72 minutes at 23 mL/min [A=0.5% (v/v) TFA; B=0.5% (v/v) TFA, 30% 2-propyl alcohol, 60% acetonitrile]. BMP-2 eluting between 18 and 20 minutes was pooled and protein concentration was determined by A280 versus 0.5% (v/v) TFA, 17% 2-propyl alcohol, and 34% acetonitrile using the theoretical extinction coefficient based upon the amino acid content. BMP-2 pool was frozen at −80° C. and subsequently lyophilized prior to refolding.

Example 3

Refolding of BMP-2 with the Non-detergent Zwitterion 3-(1-Pyridinio)-1-propanesulfonate)

Reversed-phase purified and lyophilized BMP-2 was solubilized as a 10× concentrate at 250–500 µg/ml in 20 mM reduced glutathione. Soluble protein was immediately diluted into refolding buffer producing a refolding solution containing 50 mM TRIS, 5 mM EDTA, 1 M NaCl, 1 mM oxidized glutathione, 2 mM reduced glutathione, 0.05–1.7 M 3-(1-Pyridinio)-1-propanesulfonate) and 25–50 µg/ml BMP-2 at pH 8.5. Refolding proceeded for three to four days at room temperature (approximately 20° C.).

Refolding of E. coli produced BMP-2 was analyzed under non-reducing conditions using sodium dodecyl sulfate polyacrylamide electrophoresis (SDS-PAGE). Sample aliquots were run on 10–20% acrylamide gels (Integrated Separation Systems) for approximately 2.5 hours at 75 milliamps. Protein was subsequently detected by silver stain. Refolding was scored as positive when the glutathione solubilized BMP-2 starting material appeared as a monomer of appropriate molecular weight and BMP-2 incubated in refolding media appeared as a dimer of the appropriate molecular weight under non-reducing conditions. BMP-2 dimer was also analyzed under reducing conditions by SDS-PAGE. Under reducing conditions, BMP-2 appeared as a monomer of appropriate molecular weight. Biological activity of the refolded BMP-2 was tested using the assays described in Example 11 below. BMP-2 dimer was formed at 0.05 to 1.7 M 3-(1-Pyridinio)-1-propanesulfonate); optimally at 1.0 to 1.7 M 3-(1-Pyridinio)-1-propanesulfonate).

Example 4

Refolding of BMP-2 with Nicotinic Acid (Vitamin B)

Reversed-phase purified and lyophilized BMP-2 was solubilized as a 10× concentrate at 500 µg/ml in 20 mM reduced glutathione. Soluble protein was immediately diluted into refolding buffer producing a refolding solution containing 50 mM TRIS, 5 mM EDTA, 1 M NaCl, 1 mM oxidized glutathione, 2 mM reduced glutathione, 0.25–1.0 M nicotinic acid, and 50 µg/ml BMP-2 at pH 8.5 (pH was adjusted to approximately 8.5 with 5–10 M NaOH prior to dilution of BMP-2 concentrate). The resulting solution was held at room temperature (approximately 20° C.) for three to four days.

Refolding of E. coli produced BMP-2 was analyzed under non-reducing conditions using sodium dodecyl sulfate polyacrylamide electrophoresis (SDS-PAGE) as described in Example 3. BMP-2 dimer formation was observed at 0.25 to 1.0 M nicotinic acid. Recovery of BMP-2 dimer was optimal at 1.0 M nicotinic acid.

Example 5

Refolding of BMP-2 with Pyridine-3 Sulfonic Acid

Reversed-phase purified and lyophilized BMP-2 was solubilized as described in Example 4. Soluble protein was immediately diluted into refolding buffer producing a refolding solution containing 50 mM TRIS, 5 mM EDTA, 1 M NaCl, 1 mM oxidized glutathione, 2 mM reduced glutathione, 0.25–0.60 M pyridine-3 sulfonic acid, and 50 µg/ml BMP-2 at pH 8.5 (pH was adjusted to approximately 8.5 with 5–10 M NaOH prior to addition of protein concentrate). The resulting solution was held at approximately 20° C. for three to four days.

Refolding of E. coli produced BMP-2 was analyzed under non-reducing conditions using sodium dodecyl sulfate polyacrylamide electrophoresis (SDS-PAGE) as described in Example 3. BMP-2 dimer was formed at 0.25 to 0.60 M pyridine-3 sulfonic acid. Conversion of monomeric 2 to dimer was greatest at 0.4–0.6 M pyridine-3 sulfonic acid.

Example 6

Refolding of BMP-2 with 2-(cylcohexylamino) ethanesulfonic Acid (CHES)

Reversed-phase purified and lyophilized BMP-2 was solubilized as a 10× concentrate at 250–500 µg/ml in 20 mM reduced glutathione. Soluble protein was rapidly diluted into refolding buffer. The final refolding solution contained 50 mM TRIS, 5 mM EDTA, 1 M NaCl, 1 mM oxidized glutathione, 2 mM reduced glutathione, 0.25–0.70 M 2-(cylcohexylamino)ethanesulfonic acid (CHES) and 25–50 µg/ml BMP-2 at pH 8.3. Refolding proceeded for three to four days at room temperature.

Refolding of E. coli produced BMP-2 was analyzed under non-reducing conditions using sodium dodecyl sulfate polyacrylamide electrophoresis (SDS-PAGE) as described in Example 3. BMP-2 dimer was formed at 0.25 to 0.70 M CHES. Conversion of monomeric BMP-2 to dimer was greatest at 0.70 M CHES.

Example 7

Refolding of BMP-2 with Pyrrole-2 Carboxylic Acid

Reversed-phase purified and lyophilized BMP-2 was solubilized as a 10× concentrate at 500 µg/ml in 20 mM reduced glutathione. Soluble protein was diluted into refolding buffer producing a refolding solution containing 50 mM TRIS, 5 mM EDTA, 1 M NaCl, 1 mM oxidized glutathione, 2 mM reduced glutathione, 0.40–0.65 M pyrrole-2 carboxylic acid, and 50 µg/ml BMP-2 at pH 8.4 (pH was adjusted to approximately 8.4 with 5–10 M NaOH prior to dilution of BMP-2 concentrate). The resulting solution was held at room temperature (approximately 20° C.) for three to four days.

Refolding of E. coli produced BMP-2 was analyzed under non-reducing conditions using sodium dodecyl sulfate polyacrylamide electrophoresis (SDS-PAGE) as described in Example 3. BMP-2 dimer formation was observed at 0.40 to 0.65 M pyrrole-2 carboxylic acid. Recovery of BMP-2 dimer was greatest at 0.40 M pyrrole-2 carboxylic acid.

Example 8

Refolding of BMP-13 with the Non-detergent Zwitterion 3-(1-Pyridinio)-1-propanesulfonate)

BMP-13 was expressed as described in example 1. Nine grams of frozen cell pellets obtained from the E. coli transformants as described above were thawed in 30 ml of TE8.3(100:10) buffer (100 mM Tris-HCl pH 8.3, 10 mM Na$_2$EDTA, 1 mM phenylmethylsulfonyl fluoride [PMSF]). Cells were lysed by three passes through a Microfluidizer™ [model #MCF 100 T]. The lysate was diluted to approximately 120 ml with TE8.3 100:10 buffer. A pellet of inclusion body material was obtained by centrifugation at 15,000×g. The supernatant was decanted, and the inclusion body material was suspended in 50 ml TE8.3(100:10) which also contained 1% Triton-X100. The resuspended inclusion bodies were centrifuged for 10 minutes at 15,000×g, and the supernatant was decanted. The pellet was suspended in TE8.3(20:1) buffer (20 mM Tris-HCl pH 8.3, 1 mM Na$_2$EDTA, 1 mM PMSF) which also contained 1% dithiothrietol [DTT]. After the suspension was homogenized in a Wheaton glass homogenizer, it was acidified to pH 2.5 with glacial acetic acid and then centrifuged 25 minutes at 15,000×g. The supernatant from this centrifugation was collected and chromatographed over a Sepharose S-100™ size exclusion column (83 cm×2.6 cm; ~440 ml bed) in 20 ml increments. The Sepharose S-100™ column was run with a mobile phase of 1% acetic acid at a flow rate of 1.4 ml/min. Fractions corresponding to BMP-13 monomer were detected by absorbance at 280 nm. Protein concentration was determined using a computer calculated extinction coefficient and molecular weight after measuring the absorbance of the pool at 280 nanometers. This size exclusion column pooled material was used as starting material for refolding reactions.

Alternatively, cells were lysed as above, but the initial inclusion body material pellet was dissolved in 8 M guanidine-HCl, TE8.5(100:10) buffer (100 mM Tris-HCl pH 8.5, 10 mM Na$_2$EDTA which contained 100 mM DTT, and incubated at 37° C. for 1 hour. This material was centrifuged at 12,000×g for 15 minutes at room temperature. The supernatant was injected onto C4 analytical RP-HPLC (reversed phase-high performance liquid chromatography) column (Vydac 214TP54) equilibrated to 1% B buffer (A buffer=0.1% trifluoroacetic acid [TFA], B buffer=95% acetonitrile, 0.1% TFA), with a flow rate of 1 ml/min. After 5 minutes, a linear gradient from 1% to 70% B buffer (diluted into A buffer) was run over 35 minutes, during which time the protein elutes. Protein was monitored by absorbance at 280 nm. Peak BMP-13 fractions (eluting between 25 and 35 minutes) were pooled. Protein concentration was determined by absorbance at 280 nm using the computer calculated extinction coefficient and molecular weight. This RP-HPLC C4 column pooled material was also used as starting material for refolding reactions.

BMP-13 protein in 1% acetic acid or in reverse phase buffer containing 0.1% TFA, 30–40% acetonitrile was dried or reduced in volume using a speed vacuum, redissolved as a concentrate with a few microliters of purified water or reduced glutathione, and allowed to dissolve completely for 5 to 10 minutes. Soluble protein was subsequently diluted into refolding buffer. The final refolding solution contained 50 mM TRIS, 5 mM EDTA, 1 M NaCl, 1 mM oxidized glutathione, 2 mM reduced glutathione, 1.0 M 3-(1-Pyridinio)-1-propanesulfonate) and 50 µg/ml BMP-13 at pH 8.4. Refolding proceeded for three to four days at room temperature (20–23° C.). Refolding of the E. coli produced BMP-13 in 3-(1-Pyridinio)-1-propanesulfonate) was analyzed under reducing and non-reducing conditions using 16% Tricine-sodium dodecyl sulfate polyacrylamide electrophoresis (SDS-PAGE) or 10–20% sodium dodecyl sulfate polyacrylamide electrophoresis. Protein was detected by silver stain. Refolding was scored as positive when the BMP-13 appeared as a dimer of the appropriate molecular weight under non-reducing conditions and as a monomer of appropriate molecular weight under reducing conditions. BMP-13 dimer was produced in the presence of 1.0 M 3-(1-Pyridinio)-1-propanesulfonate).

Example 9

Refolding of BMP-13 with Nicotinic Acid (Vitamin B)

Acetic acid solubilized and size exclusion purified BMP-13, as described in Example 8, was lyophilized and subsequently solubilized as a 10× concentrate at 500 µg/ml in 20 mM reduced glutathione. Soluble protein was immediately diluted into refolding buffer producing a refolding solution containing 50 mM TRIS, 5 mM EDTA, 1 M NaCl, 1 mM oxidized glutathione, 2 mM reduced glutathione,0.65–1.0 M nicotinic acid, and 50: g/ml BMP-13 at pH 8.5 (pH was adjusted to approximately 8.5 with 5–10 M NaOH prior to dilution of BMP-13 concentrate). The resulting solution was held at room temperature (approximately 20° C.) for three to four days.

Refolding of E. coli produced BMP-13 was analyzed under non-reducing conditions using sodium dodecyl sulfate polyacrylamide electrophoresis (SDS-PAGE). Sample aliquots were run on 10–20% acrylamide gels (Integrated Separation Systems) for approximately 2.5 hours at 75 milliamps. Protein was subsequently detected by silver stain. Refolding was scored as positive when the glutathione solubilized BMP-13 starting material appeared as a monomer of appropriate molecular weight and BMP-13 incubated in refolding media appeared as a dimer of the appropriate molecular weight under non-reducing conditions. Recovery of BMP-13 dimer was comparable at 0.65–1.0 M nicotinic acid.

Example 10

Refolding of BMP-2/13 Heterodimer with the Non-detergent Zwitterion 3-(1-Pyridinio)-1-propanesulfonate BMP-2 and BMP-13 were expressed as described in Example 1. BMP-2 inclusion bodies were isolated, and BMP-2 was subsequently solubilized and purified as outlined in Example 2. Reduced BMP-13 monomer was prepared as described in Example 8. Lyophilized BMP-2 was redissolved as a concentrate in purifed water. BMP-2 and BMP-13 were diluted into refolding buffer resulting in equal mass ratios in the refolding solution. The final composition of the refolding solution was 50 mM TRIS, 5 mM EDTA, 1 M NaCl, 1 mM oxidized glutathione, 2 mM reduced glutathione, 1.0 M 3-(1-pyridinio)-1-propanesulfonate), 50 µ/ml BMP-2 and 50 µg/ml BMP-13 at approximately pH 8.5. Refolding proceeded for three to four days at room temperature (20–23° C.). Refolding of the E. coli produced BMP-2/13 in 3-(1-pyridinio)-1-propanesulfonate) was analyzed under reducing and non-reducing conditions using 16% Tricine-sodium dodecyl sulfate polyacrylamide electrophoresis (SDS-PAGE) or 10–20% sodium dodecyl sulfate polyacrylamide electrophoresis. Protein was detected by silver stain. Refolding was scored as positive when the BMP-2/13 appeared as a heterodimer of the appropriate molecular weight under non-reducing conditions and as monomeric proteins of appropriate molecular weight under reducing conditions. BMP-2/13 heterodimer was produced in the presence of 1.0 M 3-(1-pyridinio)-1-propanesulfonate.

Example 11

W-20 Alkaline Phosphatase Assay

If desired for buffering purposes, a desalting step may be added prior to assay for activity of refolded protein.

W-20-17 cells are plated into 96 well tissue culture plates at a density of 10,000 cells per well in 200 µl of medium (DME with 10% heat inactivated fetal calf serum, 2 mM glutamine). The cells are allowed to attach overnight in a 95% air, 5% $CO_2$ incubator at 37° C.

The 200 µl of medium is removed from each well with a multichannel pipettor and replaced with an equal volume of test sample delivered in DME with 10% heat inactivated fetal calf serum, 2 mM glutamine and 1% penicillin-streptomycin.

The test samples and standards are allowed a 24 hour incubation period with the W-20-17 indicator cells. After the 24 hours, plates are removed from the 37° C. incubator and the test media are removed from the cells.

The W-20-17 cell layers are washed three times with 200 µl per well of calcium/magnesium free phosphate buffered saline and these washes are discarded.

50 µl of glass distilled water is added to each well and the assay plates are then placed on a dry ice/ethanol bath for quick freezing. Once frozen, the assay plates are removed from the dry ice/ethanol bath and thawed at 37° C. This step is repeated two more times for a total of 3 freeze-thaw procedures. Once complete, the membrane bound alkaline phosphatase is available for measurement.

50 µl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillation per minute.

At the end of the 30 minute incubation, the reaction is stopped by adding 100 µl of 0.2 N NaoH to each well and placing the assay plates on ice.

The spectrophotometric avsorbance for each well is read at a wavelength of 405 nanometers. These values are then compaared to known standards to give an estimate of the alkaline phospatase activity in each sample. For example, using known amounts of p-nitrophenol phosphate, absorbance values are generated. This is shown in Table I.

TABLE I

| Absorbance Values for Known Standards of P-Nitrophenol Phosphate | |
|---|---|
| P-nitrophenol Phosphate µmoles | Mean absorbance (405 nm) |
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMP-2 can be determined and converted to µmoles of p-nitrophenol phosphate cleaved per unit time as shown in Table II.

TABLE II

| Alkaline Phosphatase Values for W-20 Cells Treated with BMP-2 | | |
|---|---|---|
| BMP-2 concentration ng/ml | Absorbance Reading 405 nmeters | umoles substrate per hour |
| 0 | 0.645 | 0.024 |
| 1.56 | 0.696 | 0.026 |
| 3.12 | 0.756 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.08 |

These values are then used to compare the activities of BMP homodimer and/or heterodimer solutions to known amounts of BMP-2 homodimer.

I claim:

1. A method of expressing a protein from the transforming growth factor-beta (TGF-β) superfamily comprising:

a) culturing prokaryotic cells which have been transformed with a DNA encoding a TGF-β protein under conditions suitable for the production of recombinant TGF-β protein; and b) refolding the recombinantly produced TGF-β protein in refolding media comprising 2-aminocyclohexanecarboxylic acid.

2. The method of claim 1, wherein the prokaryotic cells are bacterial cells.

3. The method of claim 2, wherein the bacterial cells are *E. coli*.

4. The method of claim 1 wherein the protein is a bone morphogenetic protein.

5. The method of claim 1 wherein the protein is a growth and differentiatioin factor protein.

* * * * *